United States Patent [19]

Yoshikawa et al.

[11] Patent Number: 5,521,311

[45] Date of Patent: May 28, 1996

[54] 5-AMINOACETYLAMINOSULFONANILIDE COMPOUNDS

[75] Inventors: Kensei Yoshikawa; Shiuji Saito; Yohichi Shimazaki; Mariko Kashiwa; Katsuo Hatayama, all of Tokyo, Japan

[73] Assignee: Taisho Pharmaceutical Co., Ltd., Tokyo, Japan

[21] Appl. No.: 501,029

[22] PCT Filed: Feb. 16, 1994

[86] PCT No.: PCT/JP94/00228

§ 371 Date: Aug. 14, 1995

§ 102(e) Date: Aug. 14, 1995

[87] PCT Pub. No.: WO94/19318

PCT Pub. Date: Sep. 1, 1994

[30] Foreign Application Priority Data

Feb. 19, 1993 [JP] Japan .................................. 5-029550

[51] Int. Cl.$^6$ .................... C07C 311/08; C07D 295/873
[52] U.S. Cl. .................... 544/159; 514/605; 546/234; 564/99
[58] Field of Search ................ 544/159; 564/99

[56] References Cited

U.S. PATENT DOCUMENTS 3,856,857 12/1974 Beregi et al. .

FOREIGN PATENT DOCUMENTS

0641774A1 7/1992 European Pat. Off. .

Primary Examiner—Robert W. Ramsuer
Attorney, Agent, or Firm—Oblon, Spivak, McClelland, Maier & Neustadt

[57] ABSTRACT

The present compounds represented by the formula:

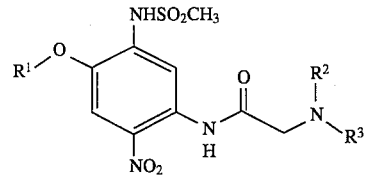

(wherein $R^1$ is a phenyl group, a halophenyl group or a cycloalkyl group having 3 to 8 carbon atoms, $R^2$ is a hydrogen atom or an alkyl group having 1 to 5 carbon atoms, $R^3$ is a hydrogen atom, an alkyl group having 1 to 7 carbon atoms, a cycloalkyl group having 3 to 8 carbon atoms, an alkenyl group having 3 to 5 carbon atoms or a benzyl group, or $R^2$ and $R^3$ are bonded together to form a 5- to 7-membered heterocycle) and salts thereof have potent anti-inflammatory, antipyretic, analgesic and anti-allergic actions with less side effects such as gastrointestinal disorders and with such a high safety as to permit long-term administration.

1 Claim, No Drawings

5-AMINOACETYLAMINOSULFONANILIDE COMPOUNDS

This application is a 371 of PCT/JP94/00228 filed Feb. 16, 1994.

TECHNICAL FIELD

The present invention relates to 5-aminoacetylaminosulfonanilide compounds having anti-inflammatory, antipyretic, analgesic and anti-allergic actions.

BACKGROUND ART

Although various sulfonanilide compounds, in particular 2-phenoxysulfonanilide compounds in the specification of U.S. Pat. No. 3,856,857, have been known, 5-aminoacetylaminosulfonanilide compounds of the present invention have not been known.

However, the above-mentioned known sulfonanilide compounds have been insufficient in drug effect.

An object of the present invention is to provide compounds having excellent anti-inflammatory, antipyretic, analgesic and anti-allergic actions.

DISCLOSURE OF THE INVENTION

As a result of extensive researches for the purpose of solving the above-mentioned problem, the present inventors have found that the purpose could be achieved by the following 5-aminoacetylaminosulfonanilide compounds, and have accomplished the present invention.

The present invention relates to the compounds represented by Formula (I):

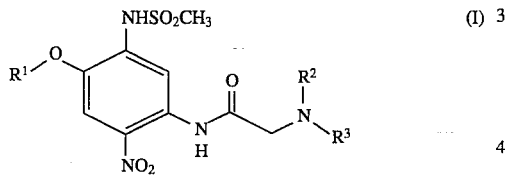

(I)

(wherein $R^1$ is a phenyl group, a halophenyl group or a cycloalkyl group having 3 to 8 carbon atoms, $R^2$ is a hydrogen atom or an alkyl group having 1 to 5 carbon atoms, $R^3$ is a hydrogen atom, an alkyl group having 1 to 7 carbon atoms, a cycloalkyl group having 3 to 8 carbon atoms, an alkenyl group having 3 to 5 carbon atoms or a benzyl group, or $R^2$ and $R^3$ are bonded together to form a 5- to 7-membered heterocycle) and salts thereof.

The halophenyl group for $R^1$ refers to a phenyl group substituted by one or two of the same or different atoms selected from the group consisting of a fluorine atom, a chlorine atom and a bromine atom, and the cycloalkyl group having 3 to 8 carbon atoms refers to a cyclopropyl group, a cyclobutyl group, a cyclopentyl group, a cyclohexyl group, a cycloheptyl group or a cyclooctyl group.

The alkyl group having 1 to 5 carbon atoms for $R^2$ refers to a methyl group, an ethyl group, an n-propyl group, an n-butyl group and an n-pentyl group.

The alkyl group having 1 to 7 carbon atoms for $R^3$ refers to a straight or branched chain alkyl group such as, for example, a methyl group, an ethyl group, an n-propyl group, an isopropyl group, an n-butyl group, an isobutyl group, an n-pentyl group, an n-hexyl group or an n-heptyl group; the cycloalkyl group having 3 to 8 carbon atoms refers to a cyclopropyl group, a cyclobutyl group, a cyclopentyl group, a cyclohexyl group, a cycloheptyl group or a cyclooctyl group; and examples of the alkenyl group having 3 to 5 carbon atoms are an allyl group, a 2-butenyl group, a 3-butenyl group and a 3-methyl-2-butenyl group.

Examples of the 5- to 7-membered heterocycle formed by bonding $R^2$ and $R^3$ together are a pyrrolidino group, a piperidino group, a hexamethyleneimino group, a morpholino group, a thiomorpholino group, a piperazino group and a 4-methylpiperazino group.

The salt refers to salts with inorganic acids such as hydrochloric acid, hydrobromic acid, sulfuric acid, nitric acid or phosphoric acid, or organic acids such as acetic acid, propionic acid, succinic acid, fumaric acid, maleic acid, benzoic acid, phthalic acid, cinnamic acid, glycolic acid, lactic acid, malic acid, tartaric acid, citric acid, methanesulfonic acid or p-toluenesulfonic acid.

Methods for preparing the compounds of the present invention are as follows:

(1) The compounds of Formula (I) of the present invention can be prepared, for example, according to a preparation method shown by the following Reaction Route (i) using 2-fluoro-5-nitroaniline as a starting material.

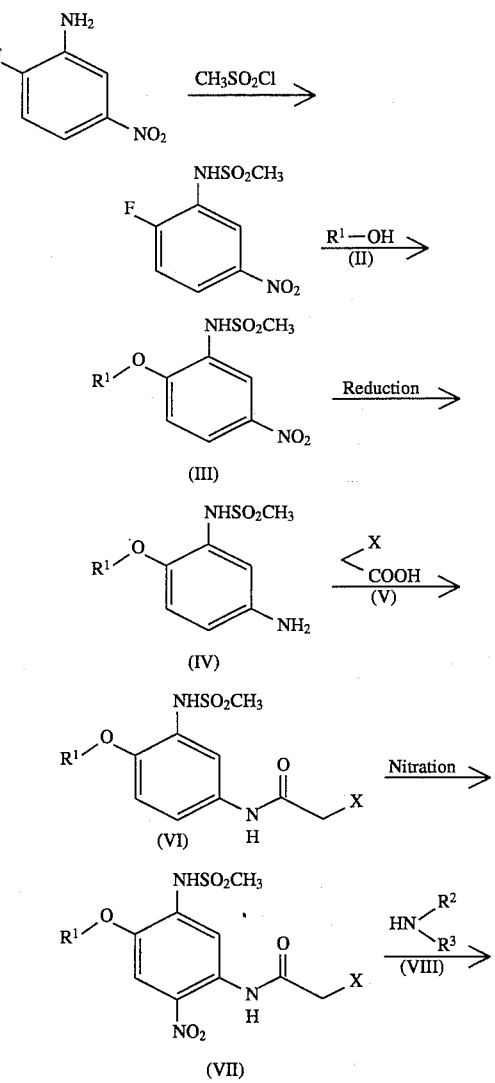

Reaction Route (i)

-continued
Reaction Route (i)

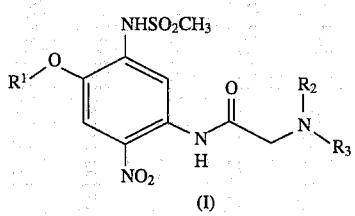

(wherein $R^1$, $R^2$ and $R^3$ are as defined above, X is a chlorine atom, a bromine atom or an iodine atom).

(a) First, the amino group of 2-fluoro-5-nitroaniline is sulfonylated by using methanesulfonyl chloride to give N-(2-fluoro-5-nitrophenyl)methanesulfonamide.

This reaction is preferably carried out in the presence of a base such as, for example, an inorganic base (e.g. lithium hydroxide, sodium hydroxide, potassium hydroxide, sodium carbonate, potassium carbonate, sodium bicarbonate or potassium bicarbonate) or an organic base (e.g. triethylamine, tri-n-butylamine, 1,5-diazabicyclo[4.3.0]-5-nonene, 1,8-diazabicyclo[5.4.0]-7-undecene, 1-methylmorpholine, 1-methylpiperidine, pyridine or N,N-dimethylaminopyridine).

In addition, this reaction is usually carried out in a solvent such as, for example, dichloromethane, chloroform, ethyl acetate, dioxane, tetrahydrofuran, ethyl ether, benzene, toluene, xylene, acetone, acetonitrile, water, pyridine, N,N-dimethylformamide or dimethyl sulfoxide.

(b) Subsequently, N-(2-fluoro-5-nitrophenyl)methanesulfonamide is etherized with a compound of Formula (II) in the presence of a base to give a compound represented by Formula (III).

Examples of the base in the reaction are an alkali metal hydroxide (e.g. lithium hydroxide, sodium hydroxide or potassium hydroxide), an alkali metal carbonate (e.g. sodium carbonate or potassium carbonate), an alkali metal bicarbonate (e.g. sodium bicarbonate or potassium bicarbonate), an alkali metal hydride (e.g. sodium hydride or potassium hydride), an inorganic base (e.g. metallic sodium or sodium amide) and an organic base (e.g. triethylamine, tri-n-butylamine, 1,5-diazabicyclo[4.3.0]-5-nonene, 1,8-diazabicyclo[5.4.0]-7-undecene, pyridine or dimethylaminopyridine).

This reaction may be carried out without solvent or in a solvent which is arbitrarily chosen from, for example, dioxane, tetrahydrofuran, ethyl ether, petroleum ether, n-hexane, cyclohexane, benzene, toluene, xylene, chlorobenzene, pyridine, N,N-dimethylformamide, dimethyl sulfoxide, water, dichloromethane or chloroform. Furthermore, the reaction can be accelerated by adding potassium iodide, tris[2-(2-methoxyethoxy)ethyl]amine, a quaternary ammonium salt (e.g. tetra-n-butylammonium chloride, tetra-n-butylammonium bromide, benzyltriethylammonium chloride, benzyltriethylammonium bromide or tricaptylmethylammonium chloride) or a crown ether (e.g. 18-crown-6 ether).

(c) Then, the nitro group of the compound of Formula (III) is reduced to give an amino derivative represented by Formula (IV).

This reaction may be a conventional reduction by which a nitro group leads to an amino group, for example, a catalytic reduction using palladium-carbon, Raney nickel or platinum as a catalyst, a reduction using iron or tin, a reduction using sodium sulfide—ammonium chloride, a reduction using sodium borohydride or lithium aluminum hydride.

The solvent to be used in the reaction can be arbitrarily chosen depending on the reduction. Generally, for example, an alcohol (e.g. methanol, ethanol or n-propanol), water, acetic acid, ethyl acetate, dioxane, tetrahydrofuran or acetonitrile can be used as the solvent.

(d) Subsequently, the amino group of the compound of Formula (IV) obtained above is subjected to an amidation with a haloacetic acid of Formula (V) or a reactive derivative thereof (e.g. an acid anhydride or an acid halide) to give a compound of Formula (VI).

When the carboxylic acid of Formula (V) is used, this reaction is preferably carried out in the presence of a condensing agent such as N,N-dicyclohexylcarbodiimide, 1-ethyl-3-(3-dimethylaminopropyl)carbodiimide hydrochloride, 1,1'-carbodiimidazole, methanesulfonyl chloride, benzoyl chloride or ethyl chloroformate.

When the reactive derivative (e.g. an acid anhydride or an acid halide) is used, the reaction is preferably carried out in the presence of a base such as, for example, an inorganic base (e.g. lithium hydroxide, sodium hydroxide, potassium hydroxide, sodium carbonate, potassium carbonate, sodium bicarbonate or potassium bicarbonate) or an organic base (e.g. triethylamine, tri-n-butylamine, 1,5-diazabicyclo[4.3.0]-5-nonene, 1,8-diazabicyclo[5.4.0]-7-undecene, 4-methylmorpholine, 1-methylpiperidine, pyridine or N,N-dimethylaminopyridine).

This reaction is usually carried out in the presence of a solvent such as, for example, dichloromethane, chloroform, ethyl acetate, dioxane, tetrahydrofuran, ethyl ether, benzene, toluene, xylene, acetone, acetonitrile, water, pyridine, N,N-dimethylformamide or dimethyl sulfoxide.

(e) The compound of Formula (VI) is nitrated by using a nitrating agent such as nitric acid or a nitrate to give a compound of Formula (VII).

Examples of the nitrating agent to be used in the nitration are sodium nitrate, potassium nitrate, ferric nitrate and urea nitrate. The solvent to be used in the reaction is preferably arbitrarily chosen depending on the nitrating agent, examples of which are acetic acid, acetic anhydride, trifluoroacetic acid, sulfuric acid, dichloromethane, chloroform, benzene, dioxane and ethanol.

(f) Finally, the halogen atom of the compound of Formula (VII) is subjected to a substitution reaction by using a compound of Formula (VIII) or its salt with an inorganic acid (e.g. hydrochloric acid, hydrobromic acid, sulfuric acid, nitric acid or phosphoric acid) or an organic acid (e.g. formic acid, acetic acid, propionic acid, oxalic acid, succinic acid, fumaric acid, maleic acid, benzoic acid, phthalic acid, cinnamic acid, glycolic acid, lactic acid, malic acid, tartaric acid, citric acid, methanesulfonic acid or p-toluenesulfonic acid) to give the compound of Formula (I) of the present invention.

This reaction is preferably carried out in the presence of a base such as, for example, an inorganic base (e.g. lithium hydroxide, sodium hydroxide, potassium hydroxide, sodium carbonate, potassium carbonate, sodium bicarbonate or potassium bicarbonate) or an organic base (e.g. triethylamine, tri-n-butylamine, 1,5-diazabicyclo[4.3.0]-5-nonene, 1,8-diazabicyclo[5.4.0]-7-undecene, 4-methylmorpholine, 1-methylpiperidine, pyridine or N,N-dimethylaminopyridine). Furthermore, the compound of Formula (VIII) to be used for the substitution can be used as a base as well.

This reaction is carried out without solvent, or preferably in a solvent such as, for example, acetone, acetonitrile, ethyl acetate, diisopropyl ether, tetrahydrofuran, dioxane, benzene, toluene, xylene, chlorobenzene, nitrobenzene, pyridine, N,N-dimethylformamide or dimethyl sulfoxide.

Furthermore, the reaction can be accelerated by adding potassium iodide, tris[2-(2-methoxyethoxy)ethyl]amine, a quaternary ammonium salt (e.g. tetra-n-butylammonium chloride, tetra-n-butylammonium bromide, benzyltriethylammonium chloride, benzyltriethylammonium bromide or tricaptylmethylammonium chloride) or a crown ether (e.g. 18-crown-6 ether).

(2) The compound of Formula (I) wherein $R^2$ and $R^3$ are each a hydrogen atom can be also prepared from the compound of Formula (IV) according to the following preparation method shown by Reaction Route (ii).

Reaction Route (ii)

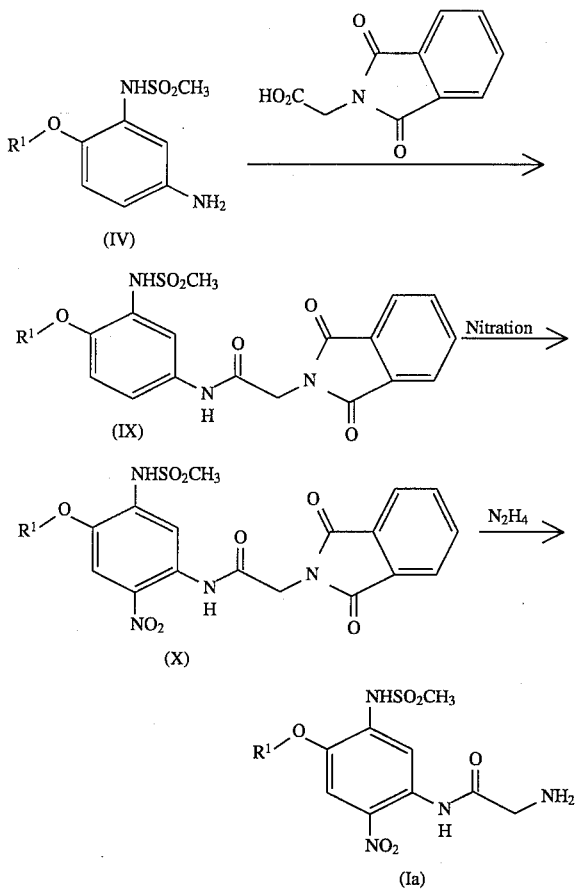

(wherein $R^1$ is as defined above).

(a) Following the same procedure as that of (1)(d) except for the use of phthaloylglycine or a reactive derivative thereof in place of the haloacetic acid or a reactive derivative thereof used in (1)(d), a compound of Formula (IX) is obtained.

(b) Then, the compound of Formula (IX) is nitrated by the same procedure as that of (1)(e) to give a compound of Formula (X).

(c) Finally, the phthaloyl group of the compound of Formula (X) is deprotected by a conventional method by which a phthaloyl group being a protective group of the amino group is deprotected, for example, a method using a hydrazine derivative (e.g. hydrazine or phenylhydrazine) to give a compound of Formula (Ia) of the present invention.

This reaction can be carried out without solvent or in a solvent such as, for example, acetonitrile, ethyl acetate, diisopropyl ether, tetrahydrofuran, dioxane, benzene, toluene, xylene, chlorobenzene, nitrobenzene, pyridine, N,N-dimethylformamide or dimethyl sulfoxide.

(3) The salt of the compound of Formula (I) of the present invention can be obtained by reacting the compound of Formula (I) with an inorganic acid or an organic acid.

Examples of the inorganic acid to be used in this reaction are hydrochloric acid, hydrobromic acid, sulfuric acid, nitric acid and phosphoric acid, and examples of the organic acid to be used in this reaction are acetic acid, propionic acid, succinic acid, fumaric acid, maleic acid, benzoic acid, phthalic acid, cinnamic acid, glycolic acid, lactic acid, malic acid, tartaric acid, citric acid, methanesulfonic acid and p-toluenesulfonic acid.

This reaction is preferably carried out in a solvent such as, for example, acetone, acetonitrile, ethyl acetate, diisopropyl ether, tetrahydrofuran, dioxane, benzene, toluene, xylene, chlorobenzene, nitrobenzene, dichloromethane or chloroform.

The compounds of the present invention can be administered orally or parenterally in conventional dosage forms.

Examples of the form are tablets, powders, granules, dusts, capsules, solutions, emulsions, suspensions and injections, and all of which can be prepared by conventional practices.

The dose for humans as an anti-inflammatory, antipyretic, analgesic or anti-allergic agent is different depending on the age, body weight, symptoms, route of administration and frequency of administration, but it is usually from 5 to 1000 mg per day.

BEST MODE FOR CARRYING OUT THE INVENTION

In order to illustrate the present invention in more detail, the following examples are given.

EXAMPLE 1

(1) To 334 ml of a pyridine solution containing 52.1 g of 2-fluoro-5-nitroaniline was added 42.1 g of methanesulfonyl chloride under ice-cooling, followed by stirring at room temperature for 7 hours. Water was added to the reaction solution, the precipitate was collected by filtration, and the crude crystals were recrystallized from ethanol to give 56.9 g of N-(2-fluoro-5-nitrophenyl)methanesulfonamide as pale yellow needles.

m.p. 128°–129° C.

(2) To 250 ml of an aqueous solution containing 73.5 g of phenol and 31.2 g of sodium hydroxide was added 50.0 g of N-(2-fluoro-5-nitrophenyl)methanesulfonamide, followed by reflux for 5 hours. To the ice-cooled reaction solution were successively added 50 ml of 36% hydrochloric acid and 200 ml of ethanol with stirring. The precipitate was collected by filtration, successively washed with ethanol and water, and air-dried to give 52.2 g of N-(5-nitro-2-phenoxyphenyl)methanesulfonamide as yellow prisms.

m.p. 112°–113.5° C.

(3) To 52.1 g of N-(5-nitro-2-phenoxyphenyl)methanesulfonamide was added 51 ml of an aqueous solution containing 2.7 g of ammonium chloride, and then 42.5 g of an iron powder was added thereto with heating at 80° C. with stirring, followed by stirring for 2 hours. To the reaction cooled to 50° C. were added ethyl acetate and water. The insoluble substances were removed by filtration, and the filtrate was extracted with ethyl acetate. The organic layer was successively washed with water and a saturated aqueous sodium chloride solution, and dried over anhydrous magnesium sulfate. The solvent was evaporated, and the residue was recrystallized from ethanol to give 29.6 g of N-(5-amino-2-phenoxyphenyl)methanesulfonamide.

m.p. 111.5°–113.5° C.

(4) To 150 ml of a dichloromethane solution containing 15.0 g of N-(5-amino-2-phenoxyphenyl)methanesulfonamide and 4.7 g of pyridine was added 6.7 g of chloroacetyl chloride under ice-cooling, followed by stirring for an hour. Water was added to the reaction solution, followed by extraction with dichloromethane. The organic layer was successively washed with water and a saturated aqueous sodium chloride solution, and dried over anhydrous magnesium sulfate. After evaporation of the solvent, the residue was recrystallized from ethyl acetate-n-hexane to give 14.4 g of N-(5-chloroacetylamino-2-phenoxyphenyl)methanesulfonamide as colorless crystals.

m.p. 126.5°–127.5° C.

(5) To 71 ml of an acetic acid solution containing 14.0 g of N-(5-chloroacetylamino-2-phenoxyphenyl)methanesulfonamide was added 4.4 g of 60% nitric acid with heating at 90° C. with stirring, followed by stirring for 20 minutes. Water was added to the reaction solution of which temperature was allowed to return to room temperature. The precipitate was collected by filtration and recrystallized from ethanol-n-hexane to give 9.3 g of N-(5-chloroacetylamino-4-nitro-2-phenoxyphenyl)methanesulfonamide as yellow needles.

m.p. 193.5°–195° C.

(6) To 7 ml of a dioxane solution containing 1.4 g of N-(5-chloroacetylamino-4-nitro-2-phenoxyphenyl)methanesulfonamide was added 0.77 g of n-butylamine at room temperature, followed by stirring for an hour. Water was added to the reaction solution, the precipitate was collected by filtration and recrystallized from ethanol to give 1.1 g of N-[5-(n-butylaminoacetylamino)4-nitro-2-phenoxyphenyl]methanesulfonamide as yellow needles.

m.p. 143°–145° C.

EXAMPLES 2 to 14

Following the same procedure as that of Example 1(6) except for using N-(5-chloroacetylamino-4-nitro-2-phenoxyphenyl)methanesulfonamide obtained by the procedures of Example 1(1) to (5) as a starting material and each of the following amines in place of n-butylamine used in Example 1(6), the compounds of the present invention shown in Table 1 were obtained.

[Amines]

n-propylamine, n-pentylamine, isopropylamine, cyclopropylamine, cyclobutylamine, cyclopentylamine, cyclohexylamine, allylamine, benzylamine, diethylamine, dipropylamine, piperidine and morpholine.

TABLE 1

| Example | $\underset{R^3}{\overset{R^2}{\underset{|}{N}}}$ | m.p. (°C.) | Solvent for Recrystallization |
|---|---|---|---|
| 2 | H-N-CH₂-CH₃ | 127–129 | ethanol |
| 3 | H-N-(CH₂)₄-CH₃ | 133–134.5 | ethyl acetate-n-hexane |
| 4 | H-N-CH(CH₃)₂ | 153.5–155.5 | ethanol |
| 5 | H-N-cyclopropyl | 169–170.5 | ethanol |
| 6 | H-N-cyclobutyl | 169.5–171 | ethanol |

TABLE 1-continued

[Structure: phenoxy group with NHSO₂CH₃, NO₂, and NHC(O)CH₂N(R²)(R³) substituents on benzene ring]

| Example | N(R²)(R³) group | m.p. (°C.) | Solvent for Recrystallization |
|---|---|---|---|
| 7 | H, N-methyl-cyclopentyl | 173–174.5 | ethanol |
| 8 | H, N-methyl-cyclohexyl | 176.5–178.5 | ethanol |
| 9 | H, N-methyl-allyl | 148.5–150 | ethanol |
| 10 | H, N-methyl-benzyl | 185–186.5 | ethanol |
| 11 | N(CH₂CH₃)(CH₂CH₃)-methyl | 103–105 | ethanol-n-hexane |
| 12 | N(CH₂CH₂CH₃)(CH₂CH₂CH₃)-methyl type | oil |  |
| 13 | N-methyl-piperidinyl | 159–160 | ethanol |
| 14 | N-methyl-morpholinyl | 171.5–173 | ethanol |

Note) Example 12: 1H-NHR (CDCl3); 0.82–0.99(6H, m), 1.38–1.65(4H, m), 2.48–2.60(4H, m), 3.25(2H, s), 3.31(3H, s), 6.97–7.09(2H, s), 7.20–7.30(1H, m), 7.38–7.49(2H, m), 7.70(1H, s), 9.15(1H, s), 11.98(1H, brs).

EXAMPLES 15 to 17

(1) Following the same procedures as those of Example 1(1) to 1(5) except for the use of 2-chlorophenol in place of phenol used in Example 1(2), N-[5-chloroacetylamino-2-(2-chlorophenoxy)-4-nitrophenyl]methanesulfonamide was obtained.

(2) Following the same procedure as that of Example 1(6) except for the use of N-[5-chloroacetylamino-2-(2-chlorophenoxy)-4-nitrophenyl]methanesulfonamide with each of n-propylamine, cyclopropylamine and allylamine in place of n-butylamine used in Example 1(6), the following compounds of the present invention were obtained.

N-[5-(n-Butylaminoacetylamino)-2-(2-chlorophenoxy)-4-nitrophenyl]methanesulfonamide
m.p. 159.5°–160.5° C.

N-[2-(2-Chlorophenoxy)-5-cyclopropylaminoacetylamino-4-nitrophenyl]methanesulfonamide
m.p. 170°–171.5° C.

N-[5-Allylaminoacetylamino)-2-(2-chlorophenoxy)-4-nitrophenyl]methanesulfonamide
m.p. 144.5°–146° C.

EXAMPLES 18 and 19

(1) To 2500 ml of a chlorobenzene solution containing 72.0 g of 60% sodium hydride were successively added 174.0 g of cyclohexanol and 10.0 ml of tris[2-(2-methoxyethoxy)ethyl]amine at room temperature, followed by stirring for 30 minutes. 136.0 g of N-(2-fluoro-5-nitrophenyl)-methanesulfonamide obtained by the procedure of Example 1(1) was added under ice-cooing, and the mixture was stirred at room temperature for 16 hours. The reaction solution, after addition of 1500 ml of 3N hydrochloric acid, was extracted with dichloromethane, and the organic layer was successively washed with water and a saturated aqueous sodium chloride solution and dried over anhydrous magnesium sulfate. After evaporation of the solvent, the residue was recrystallized from ethanol to give 131.0 g of N-(2-cyclohexyloxy-5-nitrophenyl)methanesulfonamide as pale yellow needles.

m.p. 105°–106.5° C.

(2) Reacting N-(2-cyclohexyloxy-5-nitrophenyl)methanesulfonamide in the same manners as those of Example 1(3) to (5), N-(5-chloroacetylamino-2-cyclohexyloxy-5-nitrophenyl)methanesulfonamide was obtained.

m.p. 208°–209.5° C.

(3) Following the same procedure as that of Example 1(6) except for the use of N-(5-chloroacetylamino-2-cyclohexyloxy-5-nitrophenyl)methanesulfonamide with each of n-propylamine and cyclopropylamine in place of n-butylamine used in Example 1(6), the following compounds were obtained.

N-[2-Cyclohexyloxy-5-(n-propylaminoacetylamino)phenyl]methanesulfonamide m.p. 146°–147° C.

N-(2-Cyclohexyloxy-5-cyclopropylaminoacetylaminophenyl)methanesulfonamide m.p. 198.5°–199.5° C.

EXAMPLE 20

10 ml of a dimethylformamide solution containing 1.0 g of N-(5-chloroacetylamino-4-nitro-2-phenoxyphenyl)methanesulfonamide obtained by the procedures of Example 1(1)–(5), 1.2 g of potassium iodide, 0.5 g of monomethylamine hydrochloride and 0.76 of triethylamine was stirred at room temperature for 10 hours. The reaction solution, after addition of 5 ml of 3N hydrochloric acid, was made neutral with a saturated aqueous sodium bicarbonate solution. The precipitate was collected by filtration, washed with ethyl acetate and dried to give 0.40 g of N-(5-methylaminoacetylamino-4-nitro-2-phenoxyphenyl)methanesulfonamide as yellow crystals.

m.p. 183°–184.5° C.

EXAMPLE 21

Following the same procedure as that of Example 20 except for the use of 1.1 g of monoethylamine hydrochloride in place of monomethylamine hydrochloride used in Example 20, 0.41 g of N-(5-ethylaminoacetylamino-4-nitro-2-phenoxyphenyl)methanesulfonamide was obtained as yellow crystals.

m.p. 156°–157° C.

EXAMPLE 22

(1) To 140 ml of an ethyl acetate solution containing 7.0 g of N-(5-amino-2-phenoxyphenyl)methanesulfonamide obtained by the procedures of Example 1(1) to (3) and 6.2 g of phthaloylglycine was added 1-ethyl-3-(3-dimethylaminopropyl)carbodiimide hydrochloride at room temperature, followed by stirring for 19 hours. Water was added to the reaction solution, after filtration, the collected precipitate and the filtrate were each extracted with ethyl acetate. After concentration under reduced pressure, the resulting residues were combined, washed with ethanol and dried to give 10.4 g of N-(2-phenoxy-5-phthalimidoacetylaminophenyl)methanesulfonamide as colorless crystals.

m.p. 208°–209° C.

(2) Nitrating 9.8 g of N-(2-phenoxy-5-phthalimidoacetylaminophenyl)methanesulfonamide in the same manner as that of Example 1(5), 9.6 g of N-(4-nitro-2-phenoxy-5-phthalimidoacetylaminophenyl)methanesulfonamide was obtained as pale yellow crystals.

m.p. 230°–231° C.

(3) To 350 ml of a dichloromethane-methanol (5:2) solution containing 9.5 g of N-(4-nitro-2-phenoxy-5-phthalimidoacetylaminophenyl)methanesulfonamide was added 0.64 ml of 99% hydrazine monohydrate at room temperature, followed by stirring for 19 hours. The precipitate was removed by filtration, followed by washing with hot acetonitrile. The filtrate was washed with water, and concentrated under reduced pressere. The resulting precipitate was washed with ethanol and dried to give 5.2 g of N-(5-aminoacetylamino-4-nitro-2-phenoxyphenyl)methanesulfonamide as yellow crystals.

m.p. 208°–210° C.

EXAMPLE 23

To 15 ml of an acetone solution containing 0.30 g of N-[5-(n-butylaminoacetylamino)-4-nitro-2-phenoxyphenyl]methanesulfonamide obtained by the procedure of Example 1 was added 0.06 ml of 12N hydrochloric acid, followed by stirring for 15 minutes. The precipitate was collected by filtration and washed with acetone to give 0.24 g of N-[5-(n-butylaminoacetylamino)-4-nitro-2-phenoxyphenyl]methanesulfonamide hydrochloride as yellow crystals.

m.p. 209°–211° C.

EXAMPLE 24

Following the same procedure as that of Example 23 except for the use of N-[4-nitro-5-(n-propylaminoacetylamino)-2-phenoxyphenyl]methanesulfonamide obtained by the procedure of Example 2 in place of N-[5-(n-butylaminoacetylamino)-4-nitro-2-phenoxyphenyl]methanesulfonamide used in Example 23, N-[4-nitro-5-(n-propylaminoacetylamino)-2-phenoxyphenyl]methanesulfonamide hydrochloride was obtained.

m.p. 245°–247° C.

EXAMPLE 25

Following the same procedure as that of Example 23 except for the use of N-(5-aminoacetylamino-4-nitro-2-phenoxyphenyl)methanesulfonamide obtained by the procedure of Example 22 andacetonitrile in place of N-[5-(n-butylaminoacetylamino)-4-nitro-2-phenoxyphenyl]methanesulfonamide and acetone as a reaction solvent used in Example 23, N-(5-aminoacetylamino-4-nitro-2-phenoxyphenyl)methanesulfonamide hydrochloride was obtained.

m.p. 225°–227° C.

INDUSTRIAL UTILIZATION

The compounds of the present invention have potent anti-inflammatory, antipyretic, analgesic and anti-allergic actions with less side effects such as gastrointestinal disorders, and therefore they are useful as anti-inflammatory, antipyretic, analgesic or anti-allergic agents.

The effects of the present invention are illustrated in more detail by the following experiments.

Experiment 1 [Carrageenin foot edema test]

A carrageenin foot edema test was carried out according to the method of Winter et al [Proc. Soc. Exp. Biol. Med., vol. 111, page 544 (1962)].

Six Wister strain rats (for each group) were administered orally with the test drugs [the compounds (a) to (n) of the present invention] and the control drug (indomethacin), each suspended in 5% aqueous gum arabic solution in an amount of 1 ml per 100 g of body weight. An hour later, 0.1 ml of 1% carrageenin was administered subcutaneously into the left hind foot pad. Three hours after the administration of carrageenin, the volume of the foot was determined, and the edema inhibition rate (%) was calculated for the anti-inflammatory effect.

Doses of the test drugs (a) to (l) and the control drug (indomethacin) were each 1 mg/kg, and doses of test drugs (m) and (n) were each 0.5 mg/kg.

Results are shown in Table 2.

TABLE 2

| Test drug | Edema Inhibition rate (%) | Test drug | Edema Inhibition rate (%) |
| --- | --- | --- | --- |
| a | 34.6 | i | 41.8 |
| b | 30.2 | j | 39.9 |
| c | 31.4 | k | 46.6 |
| d | 27.8 | l | 25.1 |
| e | 32.7 | m | 22.4* |
| f | 31.9 | n | 27.9* |
| g | 35.8 | indomethacin | 21.4 |
| h | 36.0 | | |

*: dose of 0.5 mg/kg
a: Compound of Example 1
b: Compound of Example 2
c: Compound of Example 5
d: Compound of Example 7
e: Compound of Example 8
f: Compound of Example 9
g: Compound of Example 10
h: Compound of Example 18
i: Compound of Example 20
j: Compound of Example 21
k: Compound of Example 22
l: Compound of Example 23
m: Compound of Example 24
n: Compound of Example 25

Experiment 2 [Adjuvant arthritis (therapy) test]

An adjuvant arthritis (therapy) test was carried out according to the method of Winder et al [Arthritis Rheum., vol. 12, page 472 (1969)].

Seven Lewis strain rats (for each group) were administered subcutaneously 0.7% *Mycobacterium tuberculosis* suspended in liquid paraffin into the left hind foot pad to induce adjuvant arthritis. 15 to 18 Days after the administration of adjuvant, rats with fully developed arthritis were administered orally with test drugs [the compound (a), (b), (i), (j), (k) and (m) of the present invention] and the control drug (indomethacin), each suspended in 5% aqueous gum arabic solution in an amount of 1 ml per 100 g of body weight once a day for 4 days.

On the day after the final administration, the volume of the foot was determined, and the edema inhibition rate (%) was calculated for the therapeutical effect. Doses of the test drugs were each 0.5 mg/kg, and dose of the control drug (indomethacin) was 1.0 mg/kg.

Results are shown in Table 3.

TABLE 3

| Test drug | Edema Inhibition rate (%) |
| --- | --- |
| a | 61.1 |
| b | 54.4 |
| i | 53.0 |
| j | 54.2 |
| k | 52.9 |
| m | 53.0 |
| indomethacin | 39.5 |

Experiment 3 [Adjuvant arthritis (pain) test]

An adjuvant arthritis (pain) test was carried out according to the method of Kuzuno et al [Chem. Pharm. Bull., vol. 23, page 1184 (1975)].

Ten Lewis strain rats (for each group) were administered subcutaneously 0.7% *Mycobacterium tuberculosis* suspended in liquid paraffin into the left hind foot pad to induce adjuvant arthritis. 15 to 18 Days after administration of adjuvant, rats with arthritis which had a squeaking response to the pain caused by stimulation of flexion and extension of the right hing foot pad, were administered orally with test drugs [the compound (a), (b), (k) and (m) of the present invention]and a control drug, each suspended in 5% aqueous gum arabic solution in an amount of 1 ml per 100 g of body weight. The occurence of squeaking response with time over 5 hours after the administration, and the inhibition rate (%) was calculated to examine the analgesic effect. Doses of the test drugs were each 1.0 mg/kg.

N-(4-nitro-2-phenoxyphenyl)methanesulfonamide was used as a control drug.

Results are shown in Table 4.

TABLE 4

| Test drug | Inhibition rate (%) |
| --- | --- |
| a | 50.6 |
| b | 47.5 |
| k | 41.9 |
| m | 52.1 |
| Control drug | 19.4 |

We claim:

1. A compound represented by the formula:

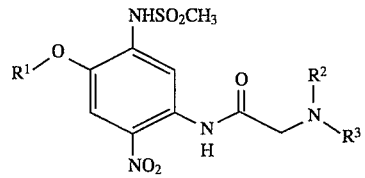

(wherein $R^1$ is a phenyl group, a halophenyl group or a cycloalkyl group having 3 to 8 carbon atoms, $R^2$ is a hydrogen atom or an alkyl group having 1 to 5 carbon atoms, $R^3$ is a hydrogen atom, an alkyl group having 1 to 7 carbon atoms, a cycloalkyl group having 3 to 8 carbon atoms, an alkenyl group having 3 to 5 carbon atoms or a benzyl group, or $R^2$ and $R^3$ are bonded together to form a 5- to 7-membered heterocycle) or salts thereof.

* * * * *